(12) United States Patent
Zhao et al.

(10) Patent No.: US 8,124,657 B2
(45) Date of Patent: Feb. 28, 2012

(54) METALLOFULLEROLS AND THEIR APPLICATIONS FOR PREPARATION OF MEDICINE FOR INHIBITION OF TUMOR GROWTH

(75) Inventors: Yuliang Zhao, Beijing (CN); Chunying Chen, Beijing (CN); Gengmei Xing, Beijing (CN)

(73) Assignee: Institute of High Energy Physics Chinese Academy of Sciences, Beijing (CN)

( * ) Notice: Subject to any disclaimer, the term of this patent is extended or adjusted under 35 U.S.C. 154(b) by 814 days.

(21) Appl. No.: 11/992,249

(22) PCT Filed: Sep. 15, 2006

(86) PCT No.: PCT/CN2006/002405
§ 371 (c)(1),
(2), (4) Date: Mar. 19, 2008

(87) PCT Pub. No.: WO2007/033578
PCT Pub. Date: Mar. 29, 2007

(65) Prior Publication Data
US 2009/0076171 A1    Mar. 19, 2009

(30) Foreign Application Priority Data
Sep. 19, 2005   (CN) .......................... 2005 1 0103494

(51) Int. Cl.
*A61K 31/047* (2006.01)
*C07C 35/00* (2006.01)

(52) U.S. Cl. ......... 514/726; 568/700; 977/736; 977/915
(58) Field of Classification Search .................. 514/726; 568/700; 977/736, 915
See application file for complete search history.

(56) References Cited

FOREIGN PATENT DOCUMENTS
CN           1480459       *   3/2004
(Continued)

OTHER PUBLICATIONS

Golub et al., Science, vol. 286, Oct. 15, 1999, pp. 531-537.*
(Continued)

*Primary Examiner* — Joseph Kosack

(57) ABSTRACT

This invention provides a composition of polyhydroxylated metallofullerene compound and its application in the preparation of antitumor pharmaceutical. In one embodiment, metallofullerol comprising the formula, $M@C_{2m}(OH)_x$, wherein M is selected from rare earth elements such as La or Gd; m is carbon atoms of 41 or 30; x is a number of hydroxyl group of from 10 to about 50. Actually, due to the reset of the neighboring hydroxyl, the numbers of O and H in Carbon cage are different, formula are thus written as $M@C_{2m}O_xH_y$. Comparing to the clinical anticancer drugs such as Paclitaxel, Cyclophosphamide, and Cisplatin, metallofullerol of $M@C_{2m}(OH)_x$ or $M@C_{2m}O_xH_y$ has superior advantages of higher antitumor efficiency, low dosage, low toxicity, and better biocompatibility.

14 Claims, 8 Drawing Sheets

FOREIGN PATENT DOCUMENTS

CN        1480459 A  *  3/2004

OTHER PUBLICATIONS

Friedman, Simon H.; Inhibition of the HIV-1 Protease by Fullerene Derivatives . . . ; J. Am. Chem. Soc. 1993, 115, 6506-6509.

Bolskar, Robert D.; First Soluble M@C60 Derivatives Provide Enhanced Access to Metallofullerenes . . . ; J. Am. Chem. Soc. 2003, 125, 5471-5478.

Dugan, Laura L.; Carboxyfullerenes as neuroprotective agents; Proc. Natl. Acad. Sci USA, vol. 94, 9434-9439; Aug. 1997 Neurobiology.

Cagle, Dawson W.; In vivo studies of fullerene-based materials using endohedral metallofullerene radiotracers; Proc. Natl. Acad. Sci USA; 96, 5182-5187, Apr. 1999,Medical.

Yamago, Shigeru; In vivo biological behavior of a water-miscible fullerene . . . ; Chemistry & Biology Jun. 1995, 2:385-389.

Chiang, Long Y.; Efficient Synthesis of Polyhydroxylated Fullerene Derivatives via . . . ; J. Org. Chem. 1994, 59, 3960-3968.

Sayes, Christie, M.; The Differential Cytotoxicy of Water-Soluble Fullerenes; Nano Letters, 2004 vol. 4, No. 10, 1881-1887.

Mirkova, Snezana M.; Nitric oxide-scavenging activity of polyhydroxylated fullerenol C60(OH)24; Nitric Oxide, 11 (2004), 201-207.

* cited by examiner

METALLOFULLEROLS AND THEIR APPLICATIONS FOR PREPARATION OF MEDICINE FOR INHIBITION OF TUMOR GROWTH

RELATED APPLICATIONS

This application is a national phase of PCT/CN2006/002405, filed Sep. 15, 2006, which claims benefits of Chinese Patent Application, CN 200510103494.7, filed Sep. 19, 2005.

FIELD OF THE INVENTION

The present invention is directed to the preparation of multihydroxylated metallofullerols and their uses for low-toxic and high-efficient anticancer medicine. Note that the term "metallofullerols" used in this document means the polyhydroxylated metallofullerenes and polyhydroxylated metallofullerene compounds.

BACKGROUND OF THE INVENTION

Malignant tumor is an important disease that threatens human health, and has become a major cause of death. In China, liver cancer, gastric cancer and breast cancer are the highest incidences among malignant tumors. Now, there are about 7.0 million deaths and 24.6 million persons living with cancer (within three years of diagnosis) in the world, there are about 1.3 million deaths in China. Beside the death, cancer has brought a big burden to family and society. Although most of the current tumor-chemotherapeutic agents, such as Epirubicin, Cyclophosphamide, Cisplatin, and Paclitaxel, are highly efficient, their therapeutic efficiency is vitally lowered by the side-effects of the drug that limits the clinic dosage and effective concentrations of therapeutic agents to tumor. To resolve this issue, new types of drug with high antineoplastic efficiency and nearly without toxicity need to develop imperatively.

As one of potential solutions to this issue, the use of nanoparticles for tumor therapy is intriguingly interesting. To realize the high efficiency and low toxicity, a potential and promising direction is to ingeniously utilize the nanoparticles whose surfaces can be adequately modified to meet the specific expectation of tumor therapy. Some nanoscale targeted-delivery devices, quantum-dots for high sensitivity examination of diseases, medical imaging and other nanoparticles, can be targeted to cancer cells. This may allow for smaller doses of toxic substances as the drugs are delivered directly to the target tissue, which has become the frontier issues.

Although fullerene ($C_{60}$), an inner-hollow, geodesic-sphere shaped molecule was first discovered in 1985 (Kroto, et al. Nature, Vol. 318, p. 162, 1985), its application in life science is limited because of very low solubility in water which leads to a low biocompatibility in living organisms. This molecule was later named buckminster fullerene in honor of Buckminster Fuller, the inventor of the geodesic dome. Typically, fullerenes each have 12 pentagons, and 20 hexagons and is classified as an icosahedron, the highest symmetry structure possible. Recent studies indicate that the properties of fullerenol molecules largely depend on the structures of the hydroxyl number and their outer modified groups (Sayes CM et al, Nano Lett, 2004, 4(10):1881-1887; Dugan L et al, Proc Natl Acad Sci USA 1997, 94: 9434-9439; Mirkova S M et al, Nitric Oxide 2004, 11:201-207; Chiang L Y et al, J Org Chem 1994, 59, 3960-3968). The lethal dose of fullerene decreased over 7 orders of magnitude with relatively minor alterations in such a surface modification (Sayes 2004). The $LD_{50}$ of $C_{60}(OH)_{24}$ is more than 5,000 ppm, while the fullerene is 20 ppb. Using C14-labelled fullerene derivative, Nakamura (1994) found it can be distributed to different tissues and organs quickly and most was enriched in liver tissue. $^{166}Ho@C_{82}(OH)_y$ could be recognized by reticuloendothelial cells and distributed to various tissues and organs except brain and fat quickly in 1 h after tail-vein injection in SD rats models (Cagle D W et al., Proc Natl Acad Sci 1999, 96:5182-5187), the concentration in each tissue was in the order of liver, bone, spleen, kidney and lung.

But in fullerene family, there are another large number of members, the atom-endohedral fullerenes. When metal(s) are encaged by the fullerene cage consisting of different carbon atoms like $C_{60}$, $C_{82}$, etc., it is called endohedral metallofullerene, including Sc, Y, Ca, Sr, Na, K, Ba, Li, Cs, Zr, and Hf. The geometric and electronic structures of endohedral metallofullerene and their physiochemical properties are quite different from the hollow fullerene like $C_{60}$, which have the potential for the application in multiple fields as organic magnet, non-linear optic materials, functional molecular switch, MRI imaging, biological isotope labeling and so on (Bolskar R D et al., J Am Chem Soc 2003; 125:5471-5478).

The metallofullerenol molecule (e.g., $Gd@C_{82}(OH)_x$) has a definite nanostructure and nanosize, and can be well characterized. In aqueous solutions, $Gd@C_{82}(OH)_x$ does not exist as an individual molecule or molecular ion but congregates into nanoparticles through large molecular interactions. These nanoparticles consist of several tens molecules whose basis is a magnetic core (Gd) and a closed carbon nano-sheath with surface modifications of hydroxyl groups (OH). Further, the outer surface of the nanoparticles is usually embraced with water molecules through hydrogen bonds, which leads the nanoparticles to have a good biocompatibility in vivo.

Currently, cancer fighting drugs are toxic to both tumor and normal cells, thus the efficacy of chemotherapy is often limited. This invention describes that the outer surface of the endohedral metallofullerenes nanoparticles is usually embraced with water molecules through hydrogen bonds, which leads the nanoparticles to have a good biocompatibility in vivo. Furthermore, these hydroxylated endohedral metallofullerenes have been found to have ability for the inhibition of the growth of tumor. The results suggest that fullerene derivatives with proper surface modifications and sizes may help realize the dream of tumor chemotherapeutics of high-efficacy and low-toxicity.

SUMMARY OF THE INVENTION

It is known that tumor tissues have more vessels than normal ones and there are number of pores at nano-size on the tumor microvascular wall, which is important for nutrient and oxygen exchange of tumor tissue from the outside. If these types of pores are blocked by the similar size of nanoparticles, the blood circulation would be jammed. Thus, cancerous tissues cannot obtain enough nutrient and further stop the growth of tumor cells. To confirm this point, the inventor designed metallofullerol compound. Its molecular size is about 1 nm. This compound has the high anti-tumor efficiency, whereas it can be aggregated and formed 1-200 nm nanoparticles at suitable sizes with a good biocompatibility. The antitumor mechanism of these nanoparticles is not due to toxic effects to cells because they do not directly kill the tumor cells, more possibly, due to jamming the pore of tumor microvessels.

This invention provides a composition of metallofullerol.

This invention provides a composition of antitumor pharmaceutical, which includes metallofullerol nanoparticles and acceptable carrier for medicine.

This invention also provides a composition of metallofullerol in the application of preparation of antitumor drugs.

To achieve the objective, this invention includes the following scheme:

Metallofullerols, comprising the formula (1)

$$M@C_{2m}(OH)_x \quad (1)$$

wherein M is chosen one metal from rare earth elements, preferably La or Gd; m is the number of carbon atoms, preferably 41 or 30; x is from 10 to 50.

This material is comprised of a metal atom incorporated into inside of its shell structure and an ordinary fullerene cage composed of carbon, while its surface is modified with many hydroxyl groups (OH) (FIG. 1). Thus, $M@C_{2m}(OH)_x$ as showed have a good biocompatibility in vivo. In the mean time, due to the existence of hydroxyl groups, metallofullerol has lower toxicity than its corresponding metallofullerene.

Actually, due to the reset of the neighboring hydroxyl, the number of O and H atoms in in the carbon cage may be different, formula are thus written as $M@C_{2m}O_xH_y$.

$$M@C_{2m}O_xH_y \quad (2)$$

In general formula, the above-mentioned metallofullerol of this invention is $M@C_{2m}(OH)_x$ (m=41 or 30 ; 10≦X<50), wherein M is La.

In general formula, the above-mentioned metallofullerol of this invention is $M@C_{2m}(OH)_x$ (m=41or 30 ; 10≦X<50), wherein M is Gd.

A tumor-inhibiting composition, include the metallofullerol with general formula $M@C_{2m}(OH)_x$, wherein M is a rare earth metal of La or Gd, m=41 or 30 and 10≦x<50.

A tumor-inhibiting composition, compromise the metallofullerol nanoparticles with general formula $[M@C_{2m}(OH)_x]_n$, wherein M is selected from a rare earth metal of La or Gd, m=41 or 30 and 10≦x<50. Letter n is the number of molecules of the metallofullerenols from which the metallofullerenols nanoparticles is formed by agglomeration, 1≦n<200.

In particular, embodiments, the metallofullerol with general formula aggregate and form nanoparticles, comprising formula $[M@C_{2m}(OH)_x]_n$. Through the selection of proper solvent, the suitable concentration, sonication and so on, the size of aggregated particles of metallofullerol ($M@C_{2m}(OH)_x$) can be controlled within 1-200 nm.

In one aspect, the intention also provides a mixture comprising proper solvent and medically-compatible carrier. The solvent may be one of water, physiological saline, Tris-HCl or phosphate buffer. The above-mentioned medically-compatible carrier is the acceptable and conventional carriers in medical science, i.e., thinner, excipient, filler, sorbent, accelerant and so on.

The tumor-inhibiting composition of this invention includes the concentration of metallofullerols between $1 \times 10^{-5}$ and 1 mmol/L. When the concentration is more than 1 mmol/L, the solubility of metallofullerols decreases and larger size particles will be easily formed. The final concentration of metallofullerols between $1 \times 10^{-5}$ to 1 mmol/L does not have obvious cytotoxicity.

Tumor that can be treated with metallofullerols comprises but not limits to lung cancer, liver cancer, gastric cancer, esophageal cancer, colorectal carcinoma, bladder cancer, breast cancer, cervical cancer, ovary cancer, human osteosarcoma, angiosarcoma, lymphosarcoma, leucocythemia, melanoma, and skin cancer.

A polyhydroxylated endohedral metallofullerene compound is prepared for the application in the inhibition of the tumor growth. The compound comprises a general formula, $[M@C_{2m}(OH)_x]_n$, wherein, M is chosen one metal from rare earth elements, preferably La or Gd, m=41 or 30, and 10≦x<50. Tumor comprises but not limits to lung cancer, liver cancer, gastric cancer, esophageal cancer, colorectal carcinoma, bladder cancer, breast cancer, cervical cancer, ovary cancer, human osteosarcoma, angiosarcoma, lymphosarcoma, leucocythemia, melanoma, and skin cancer.

This drug is available either in liquid or in lyophilized form. The drugs are made into different dosage forms, and dose of the metallofullerenols is between $5 \times 10^{-8}$ and $1 \times 10^{-2}$ mmol/kg/day for clinical, which is derived from dosage of $1 \times 10^{-6} - 2 \times 10^{-1}$ mmol/kg/day for pharmacological study on mice.

The drugs are made into different dosage forms, and the dose of the metallofullerenols is $5 \times 10^{-6} - 1.25 \times 10^{-4}$ mmol/kg/day for clinical, which is derived from dosage between $1 \times 10^{-4}$ and $2.5 \times 10^{-3}$ mmol/kg/day for pharmacological study on mice.

The antitumor composition can be used to patients through venous injection, peritoneal injection, oral administration or local drug delivery. In one preferable example of this invention, the above-mentioned composition was prepared as a solution for injection.

Comparing to the clinical anticancer drugs such as Paclitaxel, Cyclophosphamide, and Cisplatin, metallofullerol of $M@C_{2m}(OH)_x$ or $M@C_{2m}O_xH_y$ has superior advantages of higher antitumor efficiency, low dosage, low toxicity, and better biocompatibility.

BRIEF DESCRIPTION OF THE FIGURES

Various embodiments of the invention are described with reference to the figures, which are provided for the purpose of illustration only and are not intended to be limiting of the invention, the full scope of which is set forth in the claims below.

DETAILED DESCRIPTION OF THE INVENTION

In this invention, metallofullerenes of $Gd@C_{82}(OH)_x$, $Gd@C_{60}(OH)_x$, $La@C_{82}(OH)_x$, $La@C_{60}(OH)_x$ are synthesized using arc discharge method and extracted using a high-temperature and high-pressure method, the preparation method referred to China Patent No. 03146028.3. The synthesis and purification of $Gd@C_{60}$ cited Robert D. Bolskar et al (J. AM. CHEM. SOC. 2003, 125, 5471-5478.).

In one or more embodiments, $M@C_{2m}(OH)_x$ prepared according to the method of this invention, the number of the hydroxyl group is within 10 to 50, which can be determined by the concentrations of NaOH. Thus, the hydroxyl group can be controlled according to the modulation of the concentrations of NaOH. However, when x is below 10, the biocompatibility is not good. When x is more than 50, the $C_{82}$ or $C_{60}$ cage is not stable.

The hydroxyl number is crucial for its solubility in water-based solution and for clinical application, a further measurement of the hydroxyl number is performed using X-ray photoemission spectroscopy (XPS) and Synchrotron Radiation based XPS in Beijing.

The samples used in XPS experiment are deposited onto the high-purity golden substrates to obtain thin films for the XPS measurements, which is carried out at ultra vacuum chamber with background pressure of $8 \times 10^{-10}$ Torr, and about $1 \times 10^{-9}$ Torr during the measurement. The photon from synchrotron radiation was used as the excitation source. The experimental energy resolution was estimated to be about 0.5 eV. To inspect the contamination, XPS survey scans on the surface were performed before and after measurements.

To make appropriate size of $M@C_{2m}(OH)_x$ nanoparticles, $Gd@C_{82}(OH)_x$ or $Gd@C_{60}(OH)_x$ is first dissolved in physiological saline solution and sonicated for 1 min at room temperature. Then $Gd@C_{82}OH_{22}$ or $Gd@C_{60}(OH)_x$ molecules will be aggregated into nanoparticles with diameters ranging from 1-200 nm. The following examples related to metallofullerol solutions use the metallofullerol nanoparticles within the size of 1-200 nm.

Below, various examples are listed to further elucidate the invention. But, this invention is not limited to the examples described as below.

EXAMPLE 1

Synthesis and Purification of $Gd@C_{82}$

Figure 2:
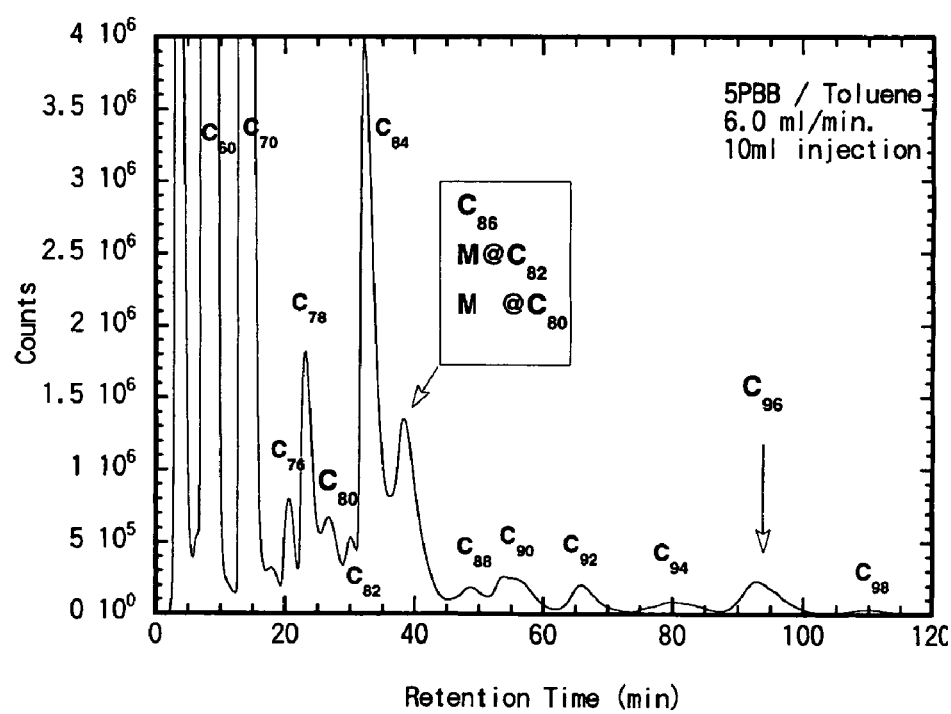
FIG. 2 is the HPLC chromatogram for $Gd@C_{2m}$ (in 5PBB columns).

The metallofullerenes are synthesized using arc discharge method and extracted using a high-temperature and high-pressure method. The starting materials are the mixture of $Gd_2O_3$ (purity>99.999%) powder and high purity graphite powder purity>99.999%), its molar ratio is Gd:C=(0.5~3): 100. The mixture of powders is first pressed into a graphite rod which is sintered at 1000-2000° C. for 24 hours and used as the electrode in the arc discharge process. Another method is to make hole with a diameter of ~20 mm in the ready graphite rod and then fill the hole with $Gd_2O_3$ powders. This $Gd_2O_3$-filled graphite rod after being sintered can also used as the electrode in the arc discharge process. The soot of the arc discharge process includes products like $Gd@C_{2m}$, $Gd_2@C_{2m}$, $Gd@C_{2n}$, $C_{60}$, $C_{70}$, etc. as shown in FIG. 2. In the syntheses processes, inert gas (like He or Ar) of 50~600 torr is used, and the discharge current is 80~500 A.

Purification of $Gd@C_{82}$ and $Gd@C_{60}$

The soot is dissolved in toluene, and reflux in toluene at 100~200° C. for 12~24 hours. Then, the products are extracted using a high-temperature and high-pressure method in DMF at 100~200° C. with 50~100 MPa, reflux for 12~24 hours. Further separation and purification of $Gd@C_{82}$ and $Gd@C_{60}$ are performed using a two-step high performance liquid chromatography (HPLC, LC908-C60, Japan Analytical Industry Co) coupling with 5PBB and then Buckyprep columns (Nacalai Co. Japan). The isolated $Gd@C_{82}$ and $Gd@C_{60}$ species were identified by the matrix-assisted laser desorption time-of-flight mass spectrometer (MADLI-TOF-MS, AutoFlex, Bruker Co., Germany).

The purity of the final $Gd@C_{82}$ and $Gd@C_{60}$ product was greater than 99.5%. The production rate of $Gd@C_{82}$ is about 10% of the weight of graphite rods used, and $Gd@C_{60}$ is 35% of the weight of the graphite rods used.

Preparation and Determination of $Gd@C_{82}(OH)_x$

The water-soluble Gd-fullerenols was synthesized by the alkaline reaction. The $Gd@C_{82}$ toluene solution (containing 1 g $Gd@C_{82}$) was first mixed with 100 ml aqueous solution containing 50% NaOH, and then several drops of catalyst of 40% TBAH (tetrabutylammonium hydroxide) were added into the reaction system. The mixture of solutions was vigorously stirred at room temperature; the color of the solution in beaker was changed from the originally deep violet into colorless, meanwhile a brown sludge precipitated onto bottom of the beaker. After adding more water into the brown sludge, it was stirring over night. The brown precipitate was washed using MeOH which was then removed by the vacuum-evaporation system. This washing manipulation was repeated several times for a complete removal of the remnant TBAH and NaOH. Finally, the brown precipitate was dissolved into deionized water with continuous stirring for 24 hrs until the solution color became a clear reddish brown. Then it was purified by a Sephadex G-25 column chromatography (5×50 cm²) with an eluent of neutralized water. The remained trace catalyst and Na⁺ ions were completely removed in this process. To obtain a final Gd-metallofullerenol product of a narrow region of distribution of the hydroxyl number, the fraction (eluate) was collected in a time interval of only several minutes.

The elemental analysis method was first used to measure the number of hydroxyl groups, giving the hydroxyl number in different samples of $Gd@C_{82}(OH)_n$, collected at different retention time. We also tried to analyze $Gd@C_{82}(OH)_n$ using MALDI-TOF-MS technique, but it is quite difficult to observe the mass peak of molecular ions, because under the laser interaction, the OH-group is easily dissociated from the cage surface. However the $Gd@C_{82}$ peaks exist in any case of analyses, indicating the high stability of this compound. This is a great merit for using it as a clinic medicine.

Preparation of $Gd@C_{60}(OH)_x$

The preparation of $Gd@C_{60}(OH)_x$ is similar with the processes of $Gd@C_{82}(OH)_x$ described above. After the separation process, the water-soluble products with purity>99.99% are freeze dryness and storage for the uses in anticancer experiments.

Synthesis of $[Gd@C_{82}(OH)_x]_n$ and $[Gd@C_{60}(OH)_x]_n$ ($1 \leq n < 200$) Nanoparticles To make appropriate size of $Gd@C_{82}(OH)_x$ or $Gd@C_{60}(OH)_x$ nanoparticles, $Gd@C_{82}(OH)_x$ or $Gd@C_{60}(OH)_x$ is first dissolved in physiological saline solution and sonicated for 1 min at room temperature. Then $Gd@C_{82}OH_{22}$ or $Gd@C_{60}(OH)_x$ molecules will be aggregated into nanoparticles with diameters ranging from 1-200 nm.

EXAMPLE 2

Figure 3:
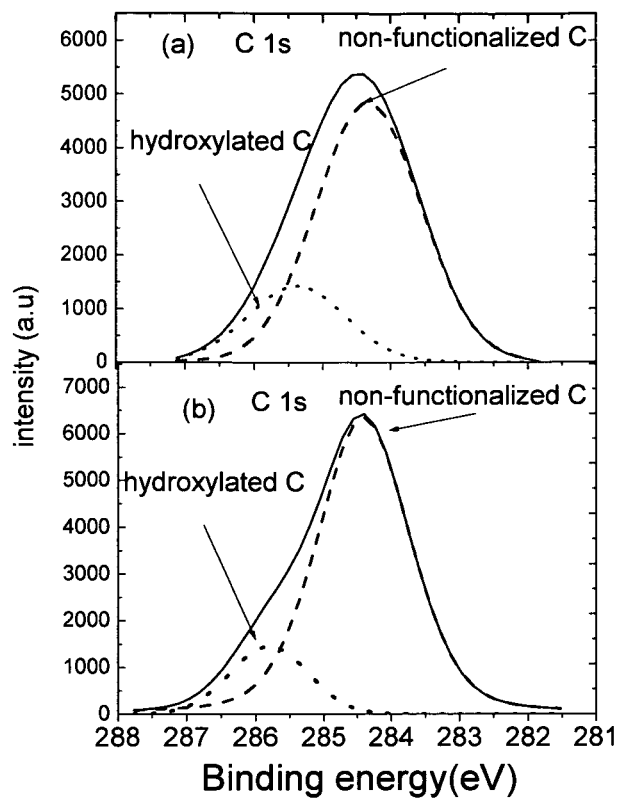
FIG. 3 is X-ray photoemission spectra for (a) $Gd@C_{82}(OH)_{22}$ and (b) $Gd@C_{82}(OH)_{12}$.

Determination of the Number of Hydroxyl Group of $Gd@C_{82}(OH)_{22}$ and $Gd@C_{82}(OH)_{12}$ X-ray photoemission spectra for $Gd@C_{82}(OH)_{22}$ (a) and $Gd@C_{82}(OH)_{12}$ (b) are shown as FIG. 3. The measurement of the hydroxyl number was performed using both commercial and synchrotron radiation X-ray photoemission spectroscopy. Through the binding energy spectra of C1s electrons for C=C and C—OH in $Gd@C_{82}(OH)_x$, intensities for the non-functionalized and hydroxylated carbons were obtained. The hydroxyl number was hence calculated from the measured intensity ratio of $sp^2$ and hydroxylated carbons.

EXAMPLE 3

Preparation of $La@C_{2m}(OH)_x$

Using the same method for $Gd@C_{82}$, the preparation of $La@C_{82}$ and $La@C_{60}$ was carried out.

(1) Synthesis of Metallofullerol $La@C_{82}(OH)_{18}$

Using NaOH alkaline method, in toluene, $La@C_{60}$ was reacted with 28% NaOH solution. After removing NaOH and other separation and purification procedures, the $La@C_{60}(OH)_{22}$ (with purity>99.9%) were obtained, which were lyophilized for use.

(2) Synthesis of Metallofullerol $La@C_{60}(OH)_{22}$

Using NaOH alkaline method, in toluene, $La@C_{60}$ was reacted with 35% NaOH solution. After removing NaOH and other separation and purification procedures, the $La@C_{60}(OH)_{22}$ (with purity>99.9%) were obtained, which were lyophilized for use.

EXAMPLE 4

Characterization of Nanoparticles

The size of $M@C_{2m}(OH)_x$ molecule is about 1 nm. However, in solution microenvironment, metallofullerol molecules are easily aggregated and formed 1-200 nm particles controlled by sonication.

The synchrotron radiation small-angle X-ray scattering (SR-SAXS), usually used for particles in the 0.5-150 nm size range, was employed to precisely determine the size of the $[Gd@C_{82}(OH)_{22}]_n$ particles in saline solution. It is performed by focusing a low divergence X-ray beam onto a solution sample and observing a coherent scattering pattern that arises from electron density in homogeneities in the saline solution of $[Gd@C_{82}(OH)_{22}]_n$. The average size of $[Gd@C_{82}(OH)_{22}]_n$ particles in saline solution was determined to be 22.0 nm.

Figure 4:
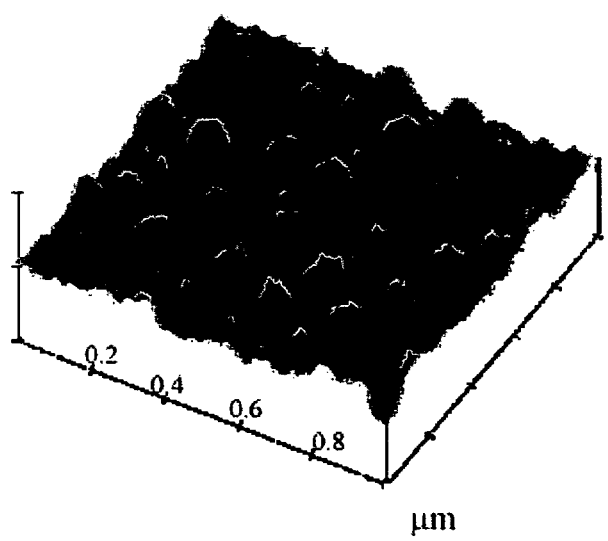
FIG. 4 is the high resolution atomic force microscopic image of $[Gd@C_{82}(OH)_{22}]_n$ nanoparticles in solution.
Figure 5:
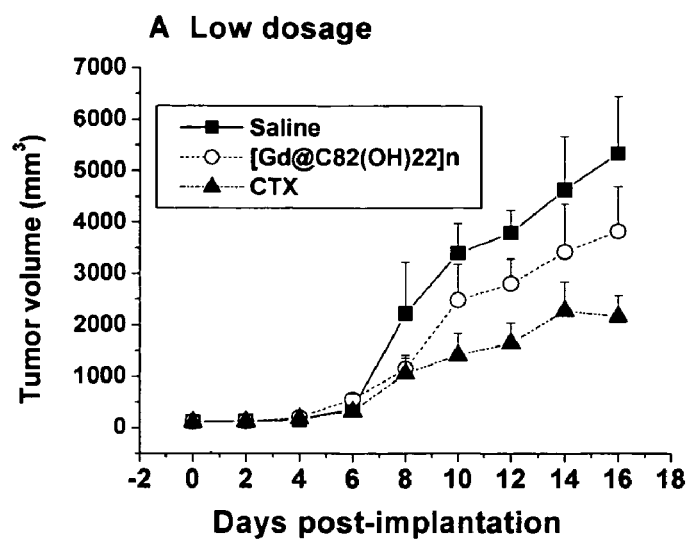
FIG. 5 is the inhibition curve of H22 hepatoma growth by treatment with $[Gd@C_{82}(OH)_{22}]_n$ nanoparticles at a lower dose.
Figure 6:
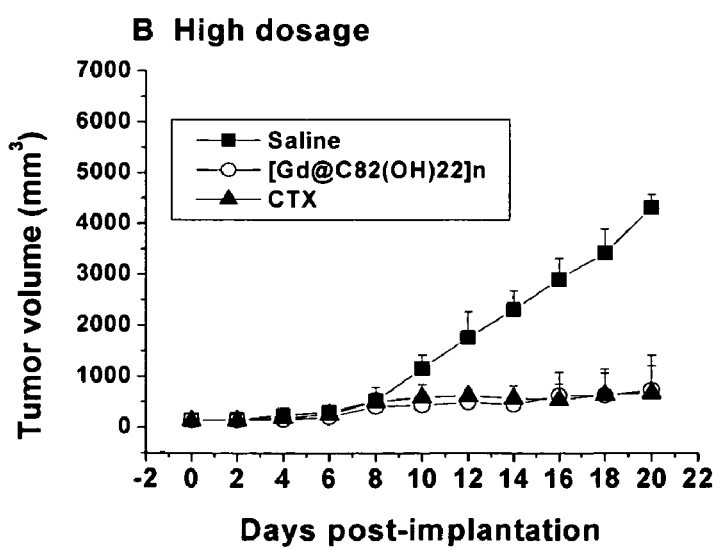
FIG. 6 is the inhibition curve of H22 hepatoma growth by treatment with $[Gd@C_{82}(OH)_{22}]_n$ nanoparticles at a higher dose.
Figure 7:
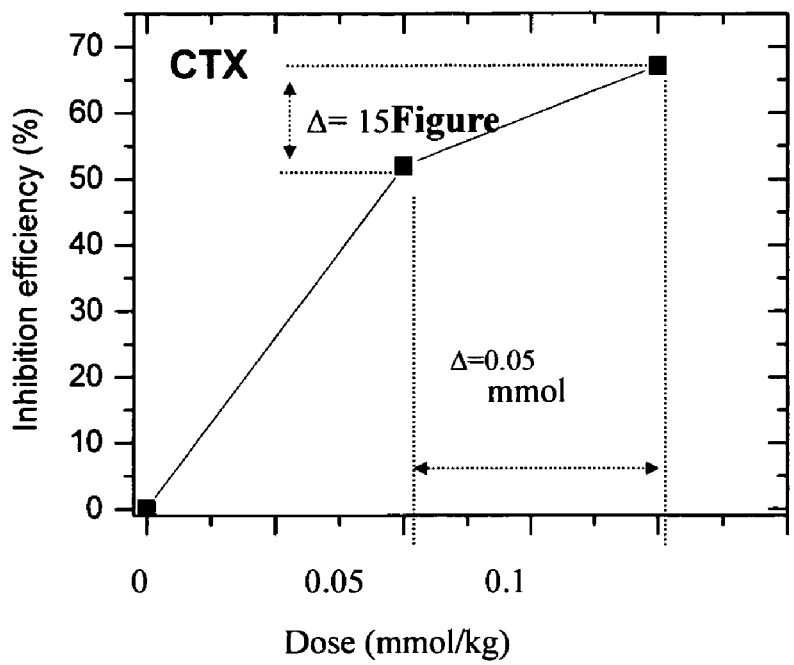
FIG. 7 is the dose-dependent inhibition efficiency of CTX on murine H22 tumor growth.
Figure 8:
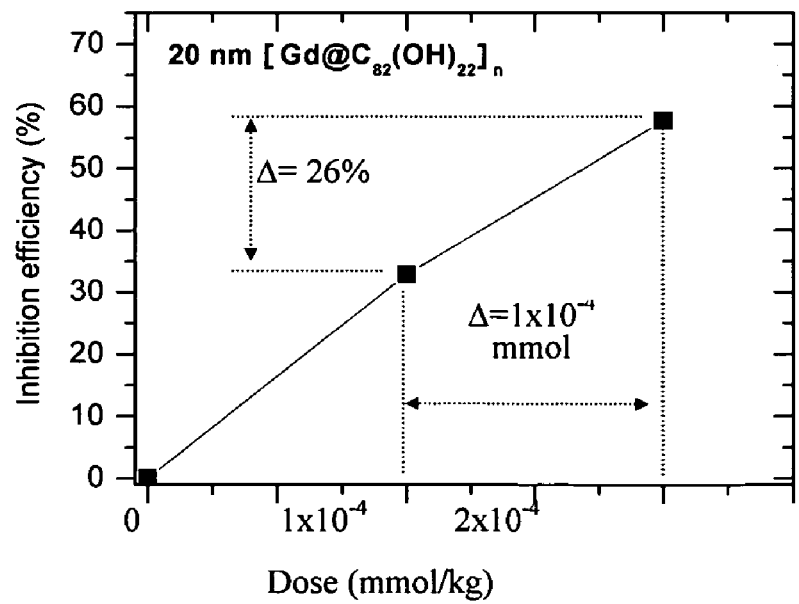
FIG. 8 is the Dose-dependent inhibition efficiency of $[Gd@C_{82}(OH)_x]_y$ on murine H22 tumor growth.

$[Gd@C_{82}(OH)_{22}]_n$ particles dissolved into saline were measured by the high resolution Atomic Force Microscopy. The average size of the particles was 22.4 nm (ranging from 0-200 nm) in diameter (FIG. 4). The two independent methods give the same results.

EXAMPLE 5

500 mg $Gd@C_{82}OH_{22}$ were dissolved in 400 ml physiological saline solution and sonicated for 1 min at room temperature. Then they were divided into 100 ampoules for injection use.

EXAMPLE 6

Antitumor studies of hydroxylated metallofullerene nanoparticles were performed on Kunming mice (female, adult, 4 weeks at the start of the experiment, body weight ranging from 20 to 22 g). The mice were subcutaneously implanted with $1\times10^6$ cells of H22 hepatoma (in 100 μl of saline) in each mouse at the right hind leg. Primary tumors (before administration of antitumor agents) were measured with calipers. The end point of the experiment was determined by the diameter of their leg loaded with tumor up to 2 or 2.2 centimeters. The size of tumor was monitored by daily measurement. Tumor growth curve was obtained by the diameter of the tumor as a function of the time.

The 40 mice of weight ranging from 20 to 22 g were randomly divided into 6 groups. The tumor-bearing mice were then systemically treated with hydroxylated metallofullerene nanoparticles saline solution by intraperitoneal injections once a day. Two doses of hydroxylated metallofullerene nanoparticles, 114 and 228 μg/kg corresponding to $1\times10^{-7}$ and $2\times10^{-7}$ mol/kg, respectively, were used in the experiment. The currently clinic antineoplastic agent CTX was used for the positive control, with a dose 30 mg/kg ($1\times10^{-4}$ mol/kg, MW 279.1) of the currently clinic use for cancer therapy. Because of its side effects, treatments by $1\times10^{-4}$ and $5\times10^{-5}$ mmol/kg of CTX continued for the first 7 days. Each mouse was administrated intraperitoneally (i.p.) a single dose of 0.2 ml per day from the second day of inoculation and continued to the day before sacrifice. The change of the tumor size was precisely measured every 24 hours.

Two different doses, $1\times10^{-7}$ and $2\times10^{-7}$ mol/kg of hydroxylated metallofullerene nanoparticles, obtained from two independent experiments, have greatly reduced the tumor weights (Table 1) and tumor volumes (FIG. 5-8) significantly.

TABLE 1

Antitumor Activity of Metallofullerol on Murine H22 Hepatoma

| Groups | Dosage | Tumor Weight (g) | Inhibition Efficiency (%) | T-test |
|---|---|---|---|---|
| Dosage I (Low) | Saline (n = 7) | 3.91 ± 0.78 | 0 | |
| | CTX ($5 \times 10^{-5}$ mol/kg/day, n = 6) | 1.80 ± 0.41 | 52.0 | P < 0.01 |
| | $Gd@C_{82}(OH)_{22}$ ($1 \times 10^{-7}$ mol/kg/day, n = 5) | 2.52 ± 0.74 | 32.9 | P < 0.01 |
| | $Gd@C_{82}(OH)_{26}$ ($1 \times 10^{-6}$ mmol/kg/day, N = 7) | 3.65 ± 1.00 | 7.7 | P < 0.01 |
| Dosage II (High) | Saline (n = 5) | 3.75 ± 0.87 | 0 | |
| | CTX ($1 \times 10^{-4}$ mol/kg/day, n = 11) | 1.22 ± 0.86 | 67.5 | P < 0.01 |
| | $Gd@C_{82}(OH)_{22}$ ($2 \times 10^{-7}$ mol/kg/day, n = 6) | 1.65 ± 1.00 | 57.7 | P < 0.01 |
| | $Gd@C_{82}(OH)_{26}$ ($2 \times 10^{-3}$ mmol/kg/day, N = 7) | 1.05 ± 0.65 | 72.0 | P < 0.01 |

Figure 1:
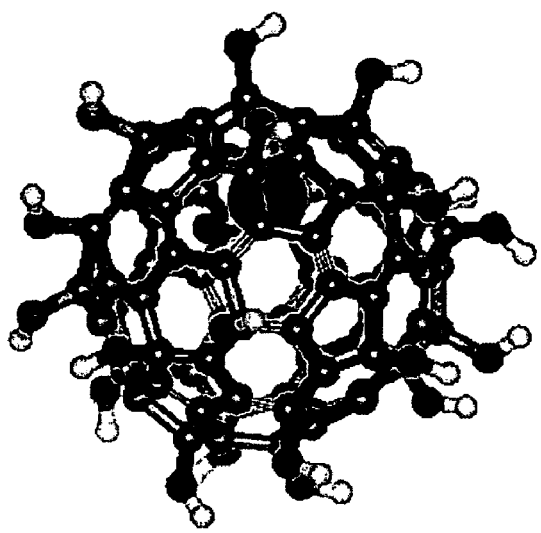
FIG. 1 is the schematic draw of the $M@C_{2m}(OH)_x$ molecule. The purple atom in the cage represents metal. The red atom out the cage represents oxygen, while the white one for hydrogen.

Table 1 is the tumor weights (mean±SEM, Table 1) from 5-7 mice in each group. FIG. 1 is the Inhibition curve of hepatoma growth in mice by treatment with metallofullerol nanoparticles in two independent experiments. The growth of tumor size was monitored through measuring the diameter of the tumor every 24 hours. Tumor volumes were then calculated according to the formula: $V=4\pi r^3/3$. Tumor growth curve was obtained by the diameter of the tumor.

In another aspect, the invention of hydrolated metallofullerene nanoparticles low toxicity in vivo. Liver function was evaluated with serum levels of total bilirubin levels (TBIL), alanine aminotransferase (ALT) and aspartate aminotransferase (AST). Nephrotoxicity was determined by blood urea nitrogen (BUN) and creatinine (Cr). For instance, the ALT levels of saline-treated groups are almost 4 times of the normal mean value. These indicate that implantation of H22 hepatoma itself in mice has harmed the functions of liver and kidney before treatments. Serum concentrations of TBIL, BUN, and Cr do not significantly changed by i.p. injections of CTX or hydrolated metallofullerene nanoparticles. After nanoparticle-treatment, the activities of ALT and AST (P<0.01) are reduced by 40% compared with saline control. Contrarily, in CTX-treated mice the serum ALT (a more specific and sensitive indicator for evaluating hepatocellular damages than AST) is not reduced, but even slightly increased (Table 2). The results suggest that, unlike CTX, hydroxylated metallofullerene nanoparticles can efficiently cease the deterioration of hepatocellular function caused by H22 hepatoma.

Table 2 is the serum TBIL, ALT, AST, and creatinine levels in tumor-bearing mice associated with metallofullerol treatment.

TABLE 2

Serum TBIL, ALT, AST, and Creatinine Levels in Tumor-Bearing Mice Associated with Metallofullerol Treatment

| Groups | TBIL (μmol/L) | ALT (IU/L) | AST (IU/L) | Creatinine (μmol/L) |
| --- | --- | --- | --- | --- |
| Saline | 1.54 ± 0.55 | 146 ± 36.3 | 888 ± 181 | 48.8 ± 3.8 |
| CTX-High | 1.66 ± 0.59 | 152.2 ± 71.5 | 337 ± 53.7 $^a$ | 51.0 ± 3.3 |
| metallo-fullerol-High dose | 1.44 ± 0.26 | 87.2 ± 32.0 $^a$ | 234 ± 27.3 $^a$ | 51.4 ± 3.6 |
| Normal mice (n = 10) | 2.20 ± 0.54 | 38.3 ± 7.0 | 142 ± 20.0 | 55.7 ± 3.0 |

Note:
$^a$ represents P < 0.01 compared with Saline group

Figure 9:
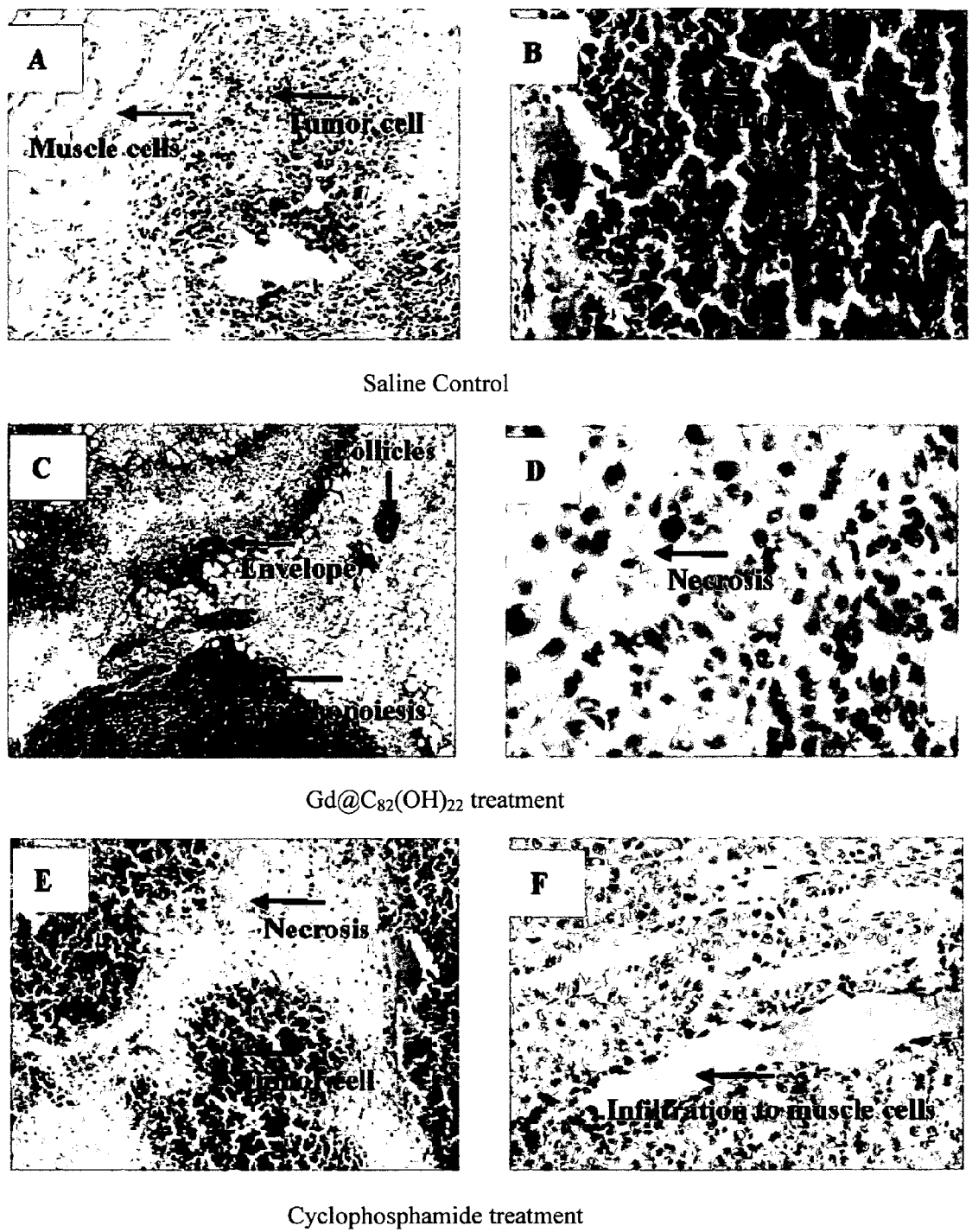
FIG. 9 represents Hematoxylin-eosin (HE) staining of the tumor tissues from the control (A and B), $[Gd@C_{82}(OH)_{22}]_n$-treated (C and D), and CTX-treated (E and F) mice.

Very interestingly, $[Gd@C_{82}(OH)_{22}]_n$ nanoparticles were observed to greatly enhance immunity and resistibility of tumor-bearing mice. The tumor morphology of HE staining of paraffin-embedded sections of tumor tissues in nanoparticle-treated, CTX-treated and the control groups, are shown in FIG. 9. In the saline control group, tumor cells heavily proliferated, arrayed regularly, and grievously invaded surrounding musculature (FIGS. 9A and B). Treatments of CTX and $[Gd@C_{82}(OH)_{22}]_n$ evidently induced tumor necrosis and hence resulted in the shrinking tumor size (FIGS. 9D-F). Surprisingly, the strong immune responses were observed in tumor tissues of $[Gd@C_{82}(OH)_{22}]_n$-treated mice (FIG. 9C), but not observed in the CTX-treated and the control groups. When spontaneous H22 liver tumors developed subcutaneously in mice, the envelope surrounding the neoplastic tissues, mainly composed of capillary vessels, fibrosis and lymphadenoid tissues were formed (FIG. 9C). Here, host lymphocyte (neutrophil cell mainly) infiltration was observed in fibroblasts and with some tumor cells inside. In the $[Gd@C_{82}(OH)_{22}]_n$-treated groups, lymphocyte hyperplasia (lymphopoiesis) and aggregated follicles around the transplanted tumor tissues were clearly seen (FIG. 9C). But in the CTX-treated mice, this envelope of fibroblasts associated with sporadic neutrophil cells was small so that it could not completely enclose the entire tumor tissues. Unlike in groups of the nanoparticle-treatment, the tumor invasion into surrounding normal muscle cells still existed in the CTX-treatment groups; although necrosis of tumor tissue was observed (FIGS. 9E and F).

The histopathological examinations of tissues and organs of the treated mice, which were performed by standard histological techniques with hematoxylin-eosin (HE) staining, revealed that treatment of hydroxylated metallofullerene nanoparticles did not produce any abnormally pathological changes on liver, spleen, kidney, heart, brain, and lung tissues.

EXAMPLE 7

Athymic BALB/c nu/nu female mice (weighing 16.0±1.0 g) were acclimated in the controlled environment (22±1° C. in temperature, 60±10% in humidity and a 12 h light/dark cycle) with free access to sterile distilled water and commercial laboratory complete food containing no pathogens. All animal experiments were performed in compliance with local ethics committee. The human beast cancer MCF-7 cell line was provided by the Cancer Institute and Cancer Hospital, Chinese Academy of Medical Sciences. The tumor bearing nude mice (female) were randomly divided into three groups, twelve in each group. In the experimental group, the mice were administered intraperitoneally (i.p.) $[Gd@C_{82}(OH)_x]_n$ saline solution once a day at the dose of 2.5 μmol/kg, after the tumor tissue implantation into the animal for 7 days, continuing until the mice were sacrificed. A currently used clinical antitumor agent, Paclitaxel, was used as the positive control. Paclitaxel was given 4 times at intervals of 3 days at the dose of 10 mg/kg; when it was not injected, saline solution was injected instead of it. 0.9% saline solution was used as a negative control in the antitumor experiment. The whole administration process lasted 14 days after the starting point. The body weight and tumor size were used as two basic parameters in the experiments, and tumor growth and body weight curve were prepared as a function of time. Tumor weight was calculated according to the formula: Tumor weight (mg)=length (mm)×(width (mm))$^2$/2.

TABLE 3

Antitumor Activity of $Gd@C_{82}(OH)_m$ on MCF-7 Human Breast Carcinoma in Nude Mice

| Group | Dosage | Inhibition Efficiency (%) |
| --- | --- | --- |
| Saline | N = 8 | |
| $Gd@C_{82}(OH)_{32}$ | 2.5 μmol/kg/day, N = 10 | 47 |
| $Gd@C_{82}(OH)_{12}$ | 1 μmol/kg/day, N = 10 | 35.6 |
| CTX | 71.6 μmol/kg/day, N = 10 | 47.0 |
| Paclitaxel | 15.2 μmol/kg/day, N = 9 | 82 |

(N represents number of mice)

There was a significant difference in tumor weight under $Gd@C_{82}(OH)_x$ treatment compared with saline treatment. Though the dose of the nanoparticle used was about one third of the Paclitaxel, nanoparticle treatment (3.8 mg/kg dose) yielded a similar reduction in tumor weight compared with Paclitaxel treatment (10 mg/kg dose). More importantly, the zero mortality of mice with $Gd@C_{82}(OH)_x$ nanoparticle treatment, while 16.7% mortality of mice with Paclitaxel treatment were observed. The tumor inhibition results obtained from animal experiments are summarized in Table 3.

EXAMPLE 8

Activity of $La@C_{82}(OH)_{18}$ on Lewis Lung Carcinoma

C57Bl/6 female mice (6-8 weeks old) were used for the Lewis Lung Carcinoma (LLC) subcutaneous model. The mice were injected subcutaneously in the right leg with 0.2 mL of cell suspension containing 5×10$^5$ LLC cells (purchased from ATCC. Tumors were allowed to grow for approximately 5 days to a volume of 100-200 mm$^3$ measured using calipers before treatment. Tumor-bearing mice were randomly divided into 3 groups for saline (control), La@$C_{82}$(OH)$_{18}$ treatment (1 μmol/kg q.d.×14 days) and CTX (71.6 μmol/kg q.d.×7days), respectively.

Figure 10:
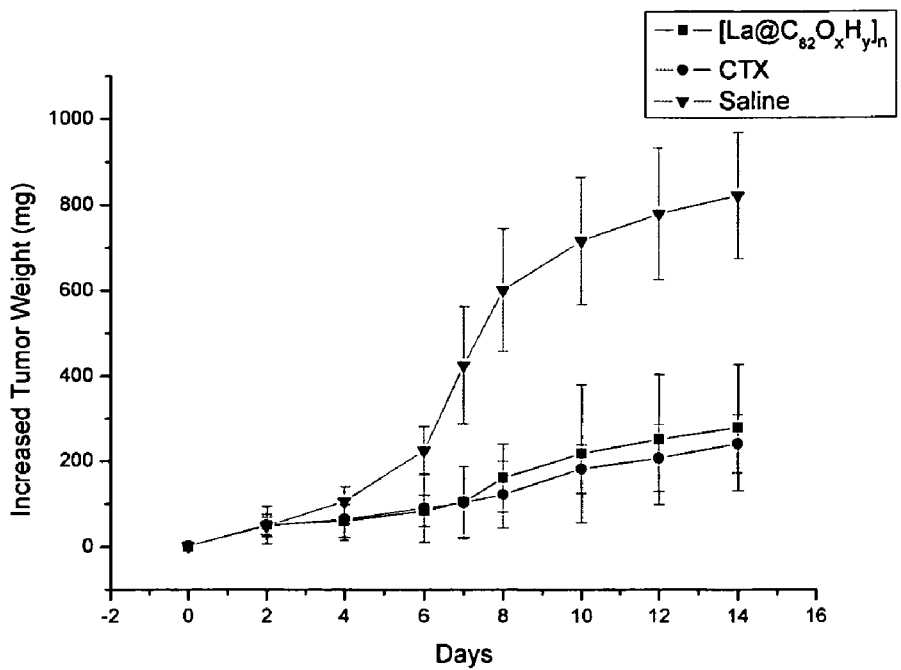
FIG. 10 is the inhibition curve of Lewis lung carcinoma growth by treatment with $La@C_{82}(OH)_{18}$

The tumor growth curves are shown in FIG. 10. La@$C_{82}$(OH)$_{18}$ nanoparticles inhibited the tumor growth significantly, which have the similar efficiency but the concentration is much lower than the clinical drug CTX.

EXAMPLE 9

Activity of Gd@$C_{60}$(OH)$_{20}$ on Lewis Lung Carcinoma

C57B1/6 female mice (6-8 weeks old) were used for the Lewis Lung Carcinoma (LLC) subcutaneous model. The mice were injected subcutaneously in the right leg with 0.2 mL of cell suspension containing 5×10$^5$ LLC cells (purchased from ATCC. Tumors were allowed to grow for approximately 5 days to a volume of 100-200 mm$^3$ measured using calipers before treatment. Tumor-bearing mice were randomly divided into 2 groups for saline (control) and Gd@$C_{60}$(OH)$_{20}$ treatment (0.5 μmol/kg q.d.×18 days), respectively.

Gd@$C_{60}$(OH)$_{20}$ nanoparticles inhibited the tumor growth significantly. Compared to the saline control, the inhibition ratio reached 42%.

EXAMPLE 10

Cytotoxicity Tests
Methods:
(1) MTT Assay for Analyzing Cell Viability After Incubation with Metallofullerols MTT [3-(4,5-dimethylthiazol-2-yl)-2,5-diphenyltetrazolium bromide] assay is a laboratory test and a standard colorimetric assay for measuring cell viability and cellular proliferation. MTT assay first described by Mosmann in 1983, is based on the ability of a mitochondrial dehydrogenase enzyme from viable cells to cleave the tetrazolium rings of the pale-yellow MTT and form dark-blue formazan crystals, which are largely impermeable to cell membranes, thus resulting in its accumulation within healthy cells.

Figure 11:
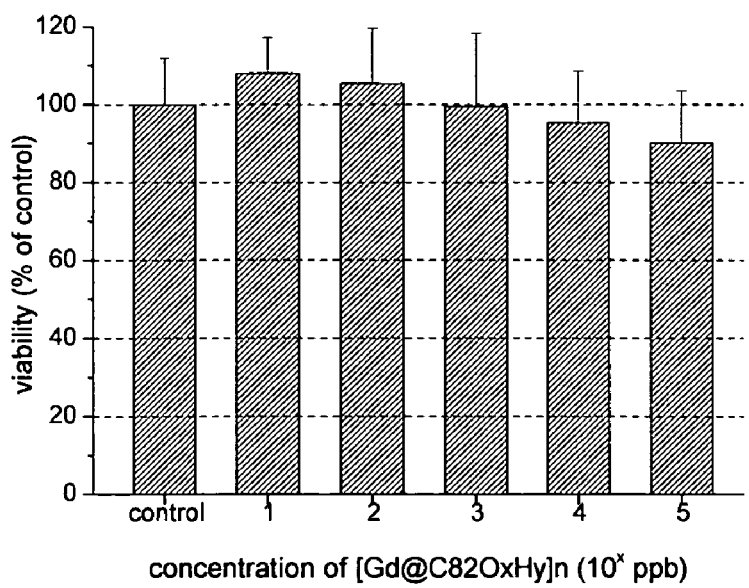
FIG. 11 shows the influence of $Gd@C_{82}(OH)_{22}$ on Cell viability of HepG2

Briefly, 5 ml 10$^5$/ml of cells were incubated in a culture flask, 24 h later, the original culture medium was replaced by 5 ml culture medium without serum. Different concentrations of metallofullerols were added into cell medium at various concentrations. After 24 h incubation, 100 μL methylthiazoletetrazolium solution (0.5 mg/mL in phosphate buffered saline) was added to each well. The plates were incubated for 3 hours at 37° C. After the incubation, 100 μL dimethyl sulfoxide was added to each well for 10 minutes at room temperature. Absorbance was measured at 570 nm using a plate reader.
(2) Flow Cytometry:Propidium Iodide (PI) Staining for Apoptic Cells 5 ml 10$^5$/ml of cells were incubated in a culture flask, 24 h later, the original culture medium was replaced by 5 ml culture medium without serum. Different concentrations of metallofullerols were added into cell medium at various concentrations. After 24 h incubation, cells were harvested, washed with physiological saline solution twice, and fixed with 70% ethanol at 4° C. The cell suspension was supplemented with 25 ppm RNase A and 50 ppm propidium iodide (PI) prior to the measurement, after washing with physiological saline solution twice and suspending. PI would not stain live cells. It would enter dead or late apoptotic cells and incorporate into DNA, thereby selectively staining the dead and late apoptotic cells into red color. The amount of apoptosis cells would be measured by the hypo-diploid peak which appeared beside the G1 peak.
Experimental Results for Cell Study:

[1] Treatment of the Human hepatic carcinoma derived cells (HepG2) with 10-10$^6$ nmol/L of Gd@$C_{82}$(OH)$_{22}$ could not result in the increase of the cell death, as shown in FIG. 11.

Figure 12:
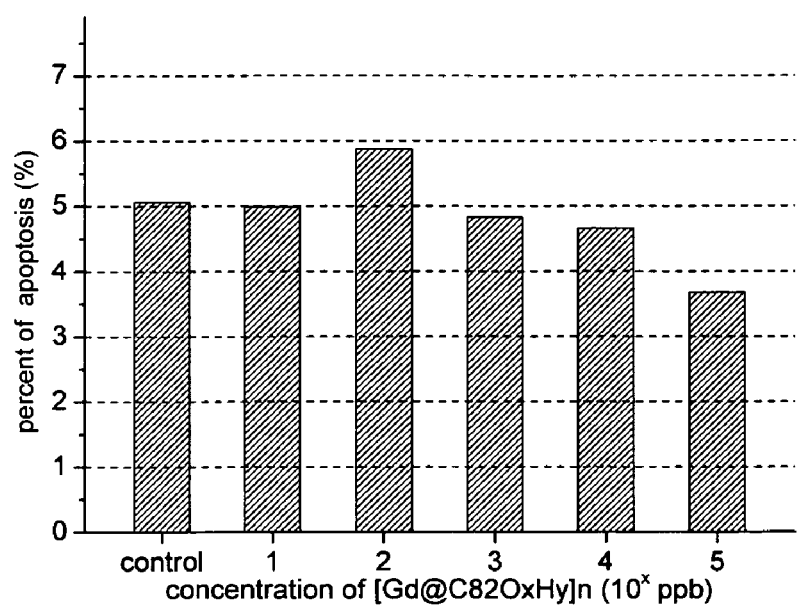
FIG. 12 shows the influence of $Gd@C_{82}(OH)_{22}$ on apoptosis of HepG2 cells.

[2] The ratio of late apoptotic or necrotic cells in the [Gd@$C_{82}$(OH)$_{22}$]$_n$-treated HepG2 is 2-4% determined by flow cytometry, which is the same as the control (FIG. 12). Thus, the results obtained from both MTT and PI staining indicated no cytotoxicity of [Gd@$C_{82}$(OH)$_{22}$]$_n$ at the tested concentrations ranging from 10-10$^6$ nmol/L.

Figure 13:
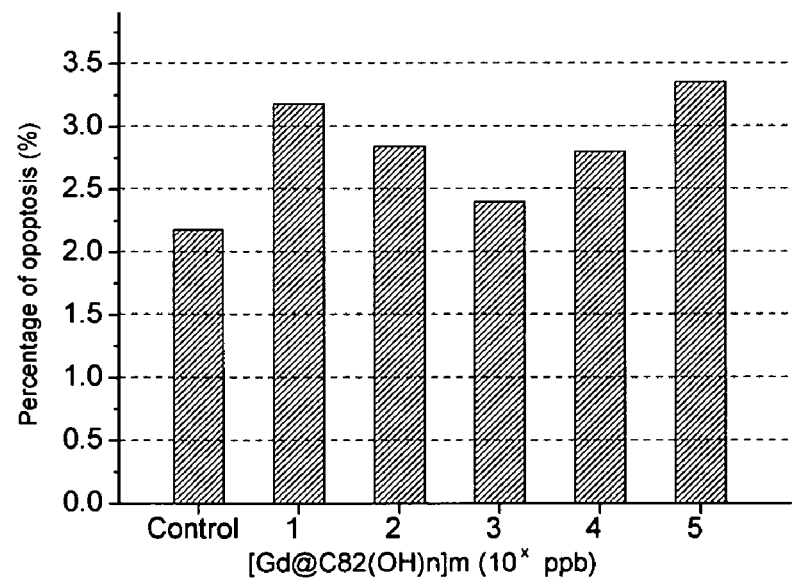
FIG. 13 shows the influence of $Gd@C_{82}(OH)_{26}$ on apoptosis of Rh35 cells

[3] The ratio of late apoptotic or necrotic cells in the Gd@$C_{82}$(OH)$_{26}$-treated Murine hepatic carcinoma cells (Rh35) is 2-4% determined by flow cytometry, which is the same as the control (FIG. 13). Thus, the results indicate that Gd@$C_{82}$(OH)$_{26}$ at the tested concentrations ranging from 10-10$^6$ nmol/L cannot induce the apoptosis of Rh35 cells.

Figure 14:
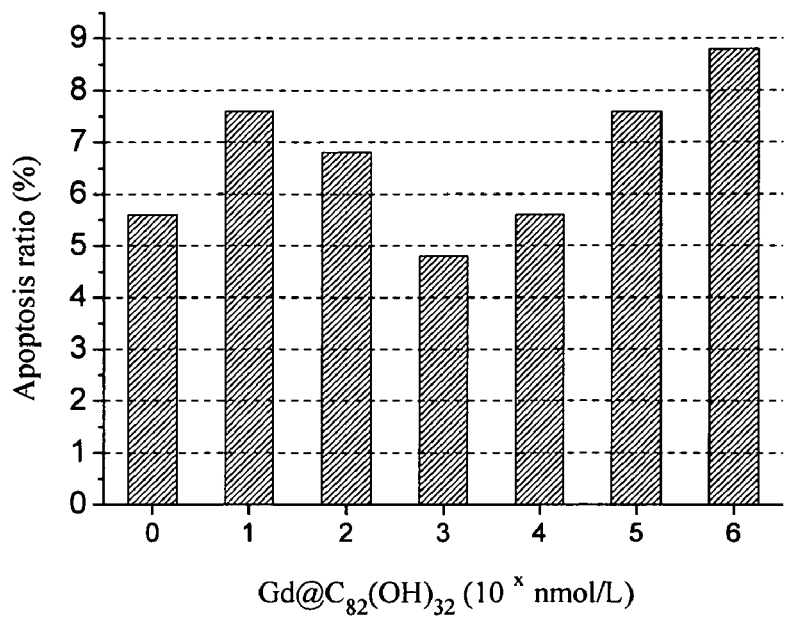
FIG. 14 Influence of $Gd@C_{82}(OH)_{32}$ on apoptosis of MCF-7 cells

[4] Cytotoxicity of Gd@$C_{82}$(OH)$_{32}$ to human breast cancer cells (MCF-7) by flow cytometry (FIG. 14) show that Gd@$C_{82}$(OH)$_{32}$ did not induce the apoptosis of MCF-7 cells at the concentration of 10-10$^6$ nmol/L. The apoptic cells are about 3.0%-9%, which are similar to the control. Gd@$C_{82}$(OH)$_{32}$ shows nearly no cytotoxicity in cancer cells.

Figure 15:
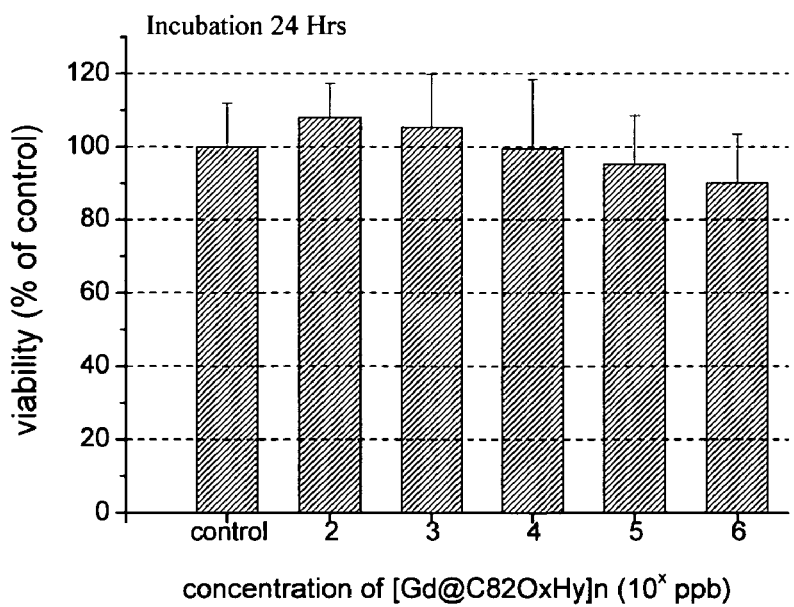
FIG. 15 shows the influence of $La@C_{82}(OH)_{20}$ on Cell viability of neuro-glioma cells.

[5] Cytotoxicity of La@$C_{82}$(OH)$_{20}$ to human neuro-gliama cells (C6) by MTT (FIG. 15) shows that La@$C_{82}$(OH)$_{20}$ has no influence on cell viability at the final concentration of 100-10$^6$ nmol/L, as shown in FIG. 15. Cytotoxicity assays using longer exposure times (48-72 hours) also gave similar results, there is no significant difference between La@$C_{82}$(OH)$_{20}$ treated cells and control.

To summarize, the above several metallofullerols show nearly no cytotoxicity in various types of cancer cells, although their hydroxyl numbers and metals are different. Unlike traditional anticancer medicines which are highly cytotoxic and cell killers, metallofullerols nanoparticles do not kill cells obviously and directly.

What is claimed is:

1. A metallofullerol, having a general formula of

$$M@C_{2m}(OH)_x$$

wherein
M is Gd or La,
m has a numerical value of 41 or 30,
x has a numerical value between 10 and 50, with the proviso that when M is Gd and when m is 41, x cannot be 40, and wherein.
$C_{2m}$ indicates a fullerene selected from $C_{82}$ or $C_{60}$, and
M@ indicates that the metal atom is incorporated inside the fullerene.

2. A tumor-inhibiting composition, comprising at least one metallofullerol according to claim 1, wherein the tumor is selected from the group consisting of lung cancer, liver cancer, and breast cancer.

3. The tumor-inhibiting composition according to claim 2, further comprising one or more of a solvent, a medically-compatible carrier, an excipient, or a combination thereof.

4. The tumor-inhibiting composition according to claim 3, wherein the solvent is one or more of water, physiological saline, Tris-HCl, and phosphate buffers.

5. The tumor-inhibiting composition according to claim 3, wherein the concentration of the metallofullerol is between 1×10$^{-5}$ and 1 mmol/L.

6. The tumor-inhibiting composition according to claim 4, wherein the concentration of the metallofullerol is between 1×10$^{-5}$ and 1 mmol/L.

7. A tumor-inhibiting composition, comprising:
metallofullerol nanoparticles for treating a tumor; wherein the metallofullerol nanoparticles can be presented by a general formula $$[M@C_{2m}(OH)_x]_n$$

wherein M is a rare earth metal atom Gd or La,
m has a numerical value of 41 or 30,
x has a numerical value between 10 and 50,
n has a numerical value between 1 and 200,
with the proviso that when M is Gd and when m is 41, x cannot be 40,
$C_{2m}$ indicates a fullerene selected from $C_{82}$ or $C_{60}$, and
M@ indicates that the metal atom is incorporated inside the fullerene, and the composition is adaptable to treat a tumor, wherein the tumor is one member selected from the group consisting of lung cancer, liver cancer and breast cancer.

8. The tumor-inhibiting composition according to claim 7, further comprising a solvent, a medically-compatible carrier, an excipient, or a combination thereof.

9. The tumor-inhibiting composition according to claim 8, wherein the solvent is selected from water, physiological saline, Tris-HCl, or phosphate buffers.

10. The tumor-inhibiting composition according to claim 8, wherein the concentration of the metallofullerol is between $1\times10^{-5}$ and 1 mmol/L.

11. The tumor-inhibiting composition according to claim 9, wherein the concentration of the metallofullerol is between $1\times10^{-5}$ and 1 mmol/L.

12. A method of treating a tumor with metallofullerol nanoparticles, comprising the steps of:
preparing a tumor-inhibiting composition comprising metollofullerol nanoparticles;
preparing a suitable dosage form of the tumor-inhibiting composition; and
treating a tumor with the tumor-inhibiting composition at a suitable concentration, the tumor is one member selected from the group consisting of lung cancer, liver cancer and breast cancer,
wherein the metallofullerol nanoparticles can be presented by a general formula $$[M@C_{2m}(OH)_x]_n$$

wherein M is a rare earth metal atom Gd or La,
m has a numerical value of 41 or 30,
x has a numerical value between 10 and 50,
n has a numerical value between 1 and 200,
$C_{2m}$ indicates a fullerene selected from $C_{82}$ or $C_{60}$, and
M@ indicates that the metal atom is incorporated inside the fullerene.

13. The method according to claim 12, wherein the concentration of the nanoparticles is between $5\times10^{-8}$ and $1.25\times10^{-2}$ mmol/kg/day.

14. The method according to claim 12, wherein the concentration of nanoparticles is between $5\times10^{-6}$ and $1.25\times10^{-4}$ mmol/kg/day.

* * * * *

UNITED STATES PATENT AND TRADEMARK OFFICE
CERTIFICATE OF CORRECTION

PATENT NO. : 8,124,657 B2
APPLICATION NO. : 11/992249
DATED : February 28, 2012
INVENTOR(S) : Yuliang Zhao et al.

Page 1 of 1

It is certified that error appears in the above-identified patent and that said Letters Patent is hereby corrected as shown below:

Column 12, Line 48, In Claim 1, delete "wherein." and insert -- wherein --, therefor.

Column 14, Line 4, In Claim 12, delete "metollofullerol" and insert -- metallofullerol --, therefor.

Signed and Sealed this
Tenth Day of July, 2012

David J. Kappos
*Director of the United States Patent and Trademark Office*